United States Patent [19]

Garito

[11] 4,431,263
[45] Feb. 14, 1984

[54] NOVEL NONLINEAR OPTICAL MATERIALS AND PROCESSES EMPLOYING DIACETYLENES

[75] Inventor: Anthony F. Garito, Radnor, Pa.

[73] Assignee: University Patents, Inc., Norwalk, Conn.

[21] Appl. No.: 129,560

[22] Filed: Mar. 12, 1980

Related U.S. Application Data

[63] Continuation-in-part of Ser. No. 52,007, Jun. 25, 1979, abandoned.

[51] Int. Cl.³ .............................................. G02B 5/172
[52] U.S. Cl. .................................................. 350/96.34
[58] Field of Search ............... 350/96.34, 96.31, 96.13; 585/534, 505

[56] References Cited

U.S. PATENT DOCUMENTS

| 3,624,406 | 11/1971 | Martin et al. | 307/88.3 |
|---|---|---|---|
| 3,694,055 | 9/1972 | Bergman, Jr. et al. | 350/96.12 |
| 3,806,226 | 4/1974 | Tien | 350/96.15 |
| 3,810,688 | 5/1974 | Ballman et al. | 350/371 |
| 3,822,928 | 7/1974 | Smolinsky et al. | 350/96.12 |
| 3,839,067 | 10/1974 | Sosnowski et al. | 350/96.12 |
| 3,923,374 | 12/1975 | Martin | 350/390 |
| 3,999,946 | 12/1976 | Patel et al. | 23/253 |
| 4,077,699 | 3/1978 | Dyott et al. | 350/96.34 |
| 4,125,534 | 11/1978 | Yee | 260/315 |
| 4,195,055 | 3/1980 | Patel | 422/56 |
| 4,195,058 | 3/1980 | Patel | 422/56 |
| 4,262,992 | 4/1981 | Berthold | 350/96.13 |

FOREIGN PATENT DOCUMENTS

| 1154191 | 6/1969 | United Kingdom . |
|---|---|---|
| 1331228 | 9/1973 | United Kingdom . |

OTHER PUBLICATIONS

Franken et al., *Reviews of Modern Physics*, vol. 35, No. 1, Jan. 1963, pp. 1179-1194, "Optical Harmonics and Nonlinear Phenomena".

Kaminow, *An Introduction to Electrooptic Devices*, Academic Press 1974.
*Physical Review Letters*, vol. 36, No. 16, Apr. 19, 1976, Baughman et al., "Optical Nonlinearities in One-Dimensional-Conjugated Polymer Crystals".
*Laser Focus*, vol. 18, No. 2, Feb. 1982, Garito et al., "Organic Crystals and Polymers-A New Class of Nonlinear Optical Materials".
*Dictionary of Organic Compounds*, vol. 3, p. 1889.
*Chemical Abstracts*, vol. 63, No. 3309 D (1965).

*Primary Examiner*—John D. Lee
*Assistant Examiner*—Frank Gonzalez
*Attorney, Agent, or Firm*—Woodcock, Washburn, Kurtz, Mackiewicz & Norris

[57] ABSTRACT

Novel nonlinear optical, piezoelectric, pyroelectric, waveguide, and other materials are presented together with processes for their employment and articles formed thereby. Such materials, processes and articles comprise diacetylenes and polymers formed from diacetylenic species, which polymers are amenable to close geometric, steric, structural, and electronic control. Accordingly, it is now possible to design, formulate and employ new diacetylenic species and polymers formed therefrom to provide nonlinear optic, waveguide, piezoelectric, and pyroelectric materials and devices having surprising efficiencies and degrees of effect. According to a preferred embodiment of the invention, diacetylenes which are crystallizable into crystals having a noncentrosymmetric unit cell may form single crystals or may be elaborated into a thin film upon a substrate by the Langmuir-Blodgett technique. Such films may, optionally, be polymerized either thermally or by irradiation for use in nonlinear optical and other systems. According to other preferred embodiments, diacetylenes are covalently bonded to substrates through the employment of silane species and subsequently polymerized to yield nonlinear optic and other devices having high structural integrity in addition to high efficiencies and effects.

17 Claims, 4 Drawing Figures

NOVEL NONLINEAR OPTICAL MATERIALS AND PROCESSES EMPLOYING DIACETYLENES

This work has been supported by funds from the Defense Advance Research Projects Agency, project designation DAAK 70-77C-0045.

RELATED APPLICATIONS

This is a continuation-in-part of Ser. No. 052,007 filed June 25, 1979, now abandoned. This is also related to copending Application Ser. No. 113,552, now abandoned, which is incorporated herein by reference.

INTRODUCTION

This invention is concerned with novel materials useful in the elaboration of thin film, single crystal and other devices; processes useful for such production, and articles formed thereby. More particularly, the invention is drawn to nonlinear optical and other materials suitable for use in electro-optical, second harmonic generating, electro-acoustic, piezoelectric, pyroelectric, waveguide, semiconductor and other devices especially those wherein arrays or aggregates of films or layers may be employed as constituents.

Thin film, single crystal and other devices such as those described above are known to those skilled in the art, as are the basic principles underlying their design, fabrication, and use. This invention is directed towards materials, especially nonlinear optical materials, which are tailored to the physical, electronic, and chemical requirements of the various devices, toward novel means for the efficient employment of such materials and toward articles which incorporate the same. Thus the requirements of symmetry, electronic configuration, physical organization, chemical bonding, and overall suitability are met by a systematic approach to design and fabrication employing a class of materials uniquely suited for maximization of these factors and effects.

The superiority of the present invention over the materials, processes and articles known to the prior art will be readily apparent. Thus for use in electro-optic, second harmonic generating and other nonlinear optical systems, the materials of this invention evidence figures of merit more than one thousand times better than the commonly used inorganic perovskites such as lithium niobate. Furthermore, certain of the materials preferred for use in accordance with the present invention are not only capable of optical second harmonic generation, but generation which is phase matchable. This property will be recognized as being highly desirable in such systems. In the piezo- and pyroelectric field, the diacetylenic species taught hereby represent a ten fold increase over lithium niobate. At the same time, the present systems may serve as waveguiding media which exhibit loss rates as low as from 0.01 to 0.1 db/km, while at the same time exhibiting unparalleled ease of fabrication. Thus, the present invention presents a single system capable of these various uses. It will be readily apparent to those skilled in art that optical switching, processing and logic devices of unparalleled performance may be fabricated employing diacetylenes according to this invention.

The compositions, processes and articles of this invention employ members of the chemical genus of diacetylenes which are molecules having at least two acetylenic bonds in conjugation with one another. It has been found by the inventor that members of this genus are uniquely suited for such employment as they possess the chemical and physical properties which may be tailored to the particular requirements of the desired systems. See in this regard the pioneering work by the inventor "Origin of the Nonlinear Second-Order Optical Susceptibilities of Organic Systems", A. F. Garito et al., *Physical Review A*, vol. 20 No. 3 pp 1179-1194 (Sept. 1979), which article is incorporated herein by reference.

More particularly, it has been found that a class of diacetylenes may be formulated which are non-centrosymmetric species, that is, which have no center of symmetry on either the molecular or crystalline unit cell level. These non-centrosymmetric species, especially those which have one or more chiral centers, find particular utility in certain embodiments of the present invention.

The term "electro-optic effect" refers to a change in the refractive index of a transparent substance induced by an applied electric field. Devices based on this effect have been used since the turn of the century for the control of light; only recently, however, has the advent of the laser stimulated great interest in the study and application of the effect and its materials implications. By various manipulations of the electric field acting upon electro-optic media, a manipulation of the transmitted light may be obtained. Thus, modulation, polarization, frequency selection, amplification, frequency modification, and other results may be observed. *An Introduction to Electro-Optic Devices* by Ivan Kaminow, (Academic Press, 1974) provides a good introduction to the field and defines some common and exemplary electro-optic and other systems both explicitly and by reference.

The phenomenon known as second harmonic generation or SHG may be seen to be a special but distinct case of the electro-optic effect. Certain materials are suited to the production of optical harmonics upon the transmission of light therethrough. The predominant harmonic which is generated in such a case is the second harmonic, thus leading to the term "second harmonic generation". This effect is described by Franken and Ward in "Optical Harmonics and Non-Linear Phenomena" Reviews of Modern Physics, 35(1) pp. 28-39 (1963).

As will be recognized by those skilled in the art, the transmission of laser light through a SHG medium will give rise to two light waves, each having frequencies which are second harmonics to the incident beam. It is difficult to utilize such second harmonic beams in most cases because the two beams may not be synchronous; they may be out of phase. In such cases, interference of "beating" is evidenced and results in output light of diminished amplitude and utility. To overcome this effect, it is highly desired to employ SHG media which are "phase matchable". Such media may generate two second harmonic waves which are synchronous, which do not show out-of-phase "beating" or interference. Such phase matchability is rare in SHG systems and is much to be preferred. With such materials, the amplitude of a resulting phase matched second harmonic is a maximum, in constant with time, and represents the highest attainable SHG efficiency for the system. Second harmonic generating systems may be devised which "cascade" light in two or more steps so that the light frequency may be doubled, then redoubled, etc. Phase matchability is important in such systems to avoid excessive power loss. Second harmonic generating materials, especially those which are phase matchable, are highly useful in signal processing, laser detection, and other devices and fields of use.

An additional phenomenon which is related to the electro-optic effect is the electro-acoustic effect. This phenomenon employs an acoustic signal to modulate an electric field experienced by an electro-optic device. Said signal, may, thus, be replicated in the transmitted light which becomes a suitable means for transmission of the signal. Those skilled in the art will recognize that other effects are known to be similar or related to the electro-optic effect and that such effects which are collectively know as nonlinear optical effects, and devices employing them are believed to be attainable through employment of one or more of the materials or processes of this invention; no limitation is therefore, to be implied from this necessarily limited discussion.

It is only recently that the nonlinear optic effects such as electro-optic and related effects have come to be understood in a nonempirical fashion. The inventor of this invention was the first to understand the physical and theoretical principles which underly nonlinear behavior in organic systems. In this regard, reference is made to "Origin of the Nonlinear Second-Order Optical Susceptabilities of Organic Systems" by Garito, et al, *Physical Review A*, Vol. 20, No. 3, PP. 1179-1194, Sept. 1979, which has been incorporated herein by reference. This understanding has enabled the design of materials and processes which are ideally suited to the requirements of electro-optic and related nonlinear optical systems.

Additional applications for the materials and processes of this invention which do not primarily rely upon nonlinearity are found in the areas of piezo- and pyroelectricity. Piezoelectricity, is a phenomenon whereby kinetic energy and electrical potential may be intercoupled through the intermediation of a suitable piezoelectric medium. The pyroelectric effect is manifested by a transformation between thermal and electrical energies through a pyroelectric medium. In practice, a piezoelectric device translates a physical stress into a current, or a current into a physical movement. It will be understood that ordinary phonographic "pickups" are common embodiments of the former phenomenon while certain audio speakers exemplify the latter. Pyroelectric devices are useful in, inter alia, temperature sensing, power generation and related applications. Both emobodiments may benefit from use of the present invention; both will profit by the advantages and efficiencies available therewith.

The invention may also be employed in the formation and fabrication of optical waveguides. Such guides are capable of perpetuating a standing light wave through the guide, and of allowing said wave to be directed, manipulated and bent. While many waveguiding systems are known, the materials of the present invention have a very high suitability for inclusion in such systems. Specifically, they evidence an excellently low loss rate of from about 0.1 to 0.01 db/km, a figure which compares favorably with commonly employed organic species and which easily outshines perovskite type compositions which are known to exhibit losses of from 5-10 db/km.

It will be understood that the foregoing is not intended to be a rigorous definition of the electronic, optic, electro-optic and other fields wherein the present invention may be employed, but, rather is intended as merely an illustrative explanation of certain of those fields. Those skilled in the art will readily appreciate the wide applicability of the materials and processes taught hereby and will understand that any electronic, optical, electro-optic, SHG, electro-acoustic, piezoelectric, pyroelectric, waveguide, semiconductor and other system which may benefit from close control of symmetry, steric, electronic, and physical elements of the constituent components will benefit through employment of this invention and that all such systems are envisioned hereby.

As will be discussed more fully below, nonlinear optic, piezo-, and pyroelectric systems are well known to require certain types of asymmetry on the molecular and crystalline unit cell level. In addition, however, it has now been discovered that electro-optic, second harmonic generating and other nonlinear optic materials required additional properties for optimization of nonlinear effects. See in this regard the *Physical Review A* article which has been incorporated herein by reference. Thus it has been found that a delocalized pi electronic system together with a suitable electronic ground and excited state manifold structure are required for good performance in organic nonlinear optic systems. It is believed that the presence of a delocalized pi electronic system makes electronic excitations more accessible for interaction with electromagnetic energy; this is reflected in the susceptibility terms of the nonlinear optical calculations presented in the *Physical Review* paper. Thus a delocalized pi electron system is believed to be vital to the efficient coupling of light with the nonlinear optical materials. The requirement for a suitable electronic manifold is related to the desirability of having a large difference in the ground state and excited state dipoles of nonlinear optical materials. This large difference is reflected in a large transition moment associated with electronic excitation and a concomitantly large nonlinear effect being associated with that transition. The diacetylenic system has now been shown to possess an ideal delocalized pi electronic system for nonlinear optical use. Furthermore, the system has an appropriate electronic manifold and is amenable to substitution with species which improve the manifold configuration still further.

The asymmetries demonstrated by certain classes of diacetylenes lend the molecules to employment in piezoelctric and pyroelectric devices as well. Additionally, diacetylenes may be extremely useful constituients of optical wave guides. This application, which does not necessarily require asymmetric discetylenes, may be employed inter alia to interconnect pluralities of nonlinear optical devices or the like to result in integrated optical switching circuit arrays and similar articles.

It is, therefore, an object of this invention to provide novel materials employing diacetylenes for inclusion in thin film or single crystal nonlinear optical and other devices. A further object is to provide processes suitable for the elaboration and construction of such devices and for other uses. A still further object is to furnish thin film, single crystal and other devices which are suitable for use as electro-optic, second harmonic generating, electro-acoustic, other nonlinear optic, piezoelectric, pyroelectric, wave guide, semiconductor and other devices. Another object is to provide nonlinear optical systems which possess excellent pi electron and electronic manifold systems. Other objects are attained by the development of diacetylenic materials and processes whereby high efficiency, productivity and effects may be achieved in device fabrication and whereby a systems approach to such fabrication may be had.

As has been indicated, materials suitable for use in nonlinear optical systems must meet certain requirements of symmetry and electronic structure. Similarly, piezo-, and pyroelectric materials must satisfy certain symmetry conditions, while compositions suitable for waveguiding and other uses have no particular symmetry or electronic requirements. The materials of this invention offer the practitioner in the art a great deal of flexibility in design and fabrication of these various devices by virtue of the ability to control closely the electronic and symmetry components of the system.

The symmetry requirements for nonlinear optical materials have been recognized empirically. See *Physical Properties of Crystals* by J. F. Nye (Oxford U.P. p. 2957, 1976); A. Yariv, *Quantum Electronics* (Wiley, 1967); *Molecular Crystals and Molecules,* A. I. Kitaigorodsky (Academic, 1973); and the Kaminow work cited previously. Thus it is known that nonlinear optical materials such as electro-optic, SHG, electro-acoustic, etc. must exhibit non-centrosymmetry. This requirement is shared by piezo-, and pyroelectric materials and, indeed, it is recognized that nonlinear optical materials are, of necessity, piezoelectric and pyroelectric as well. In this context, non-centrosymmetry refers to a state of having no center of inversion symmetry on both the molecular and unit cell basis. Thus, suitable non-centrosymmetric species not only are molecules which are asymmetric, but also are molecules which, when coalesced into a crystalline matrix, are also not symmetric vis-a-vis the unit cell of the crystal.

It is believed that the asymmetry of the unit cells is manifested by finite electronic dipoles in the materials. Such dipoles are believed to be necessary for interaction with an applied electric field; without such dipoles, coupling of the materials with an applied electric field is thought to be impossible.

It will be appreciated that molecules which are asymmetric on the molecular scale will tend to form symmetric crystalline unit cells; even many chiral molecules are known to so crystallize. It is, therefore, necessary to inquire as to symmetry on the crystal unit cell level to determine the presence or absence of non-centrosymmetry and, hence, the suitability of materials for nonlinear optical, piezo-, and pyroelectric use.

While molecules having one or more chiral centers are, necessarily, non-centrosymmetric on the molecular level and, hence, are fruitful candidates for overall non-centrosymmetry as well, species which are not chiral may also form non-centrosymmetric cells. All such materials are contemplated for use in this invention.

While symmetry considerations, thus, play a major role in selection of nonlinear optical, piezoelectric and pyroelectric materials, waveguiding and other uses for the materials, processes and articles of this invention may employ symmetric species.

As has been suggested above, the electronic structure of the materials used in the design and construction of the thin film, single crystal and other devices is of great importance to the performance of these devices. It has been discovered by this inventor that the natures of the ground state and excited state electronic manifolds of a material have large impacts on the properties possessed by said materials in optical, electronic, electro-optical and other devices. Thus it has been found that for high electro-optic, SHG, electro-acoustic, and other nonlinear optical effects a material must possess not only the requisite asymmetry but also a suitable delocalized pi electronic system. Furthermore, the ground and excited states must have a large charge separation as evidenced by large dipole moments and transition moments. The materials of the present invention have been found to possess ground state pi electronic systems which are ideally suited for devices employing such effects. Furthermore, the materials of the invention may be designed so as to have the necessary charge separation in the excited state manifold so as to result in electro-optic, SHG, and related effects of unprecedented magnitude. The processes taught by this invention are also ideally suited for fabrication of such devices in that extreme regularity can be maintained together with close orientation and tolerance control. Similar considerations clarify the utility of these materials and process in the piezoelectric, pyroelectric, waveguide, and other fields where close control of symmetry and structure are also highly beneficial.

DESCRIPTION OF THE PRIOR ART

Materials commonly employed in electronic, optic, electro-optic, piezoelectric, waveguide, semiconductor and similar materials are usually inorganic. Thus, perovskites such as niobates, tantalates and the like are known for certain of such uses while glasses such as doped silica are known for use in others. Those skilled in the art will recognize that many inorganic species may be employed for the elaboration and construction of these devices. See, for example, U.S. Pat. Nos.: 3,407,309 issued to Miller; 3,447,855 issued to Skinner; 3,624,406 issued to Martin; 3,695,745 issued to Furukawa; 3,801,688 issued to Ballman, 3,874,782 issued to Schmidt, and 3,923,374 issued to Martin.

In addition, certain species of organic materials are known for some of these various uses. Thus polyvinylidene fluoride is known to have electro-optic, SHG, and piezoelectric effects while polysiloxanes are known for use as waveguides and piezoelectric media. In all of these cases, however, the organic materials are known to evidence generally small effects; with correspondingly small effects demonstrated by the devices employing them. The materials and processes of the present invention possess properties far in advance of such known materials and, therefore, are clearly distinguishable therefrom both in terms of activity and in terms of structure.

SUMMARY OF THE INVENTION

Figure 1:
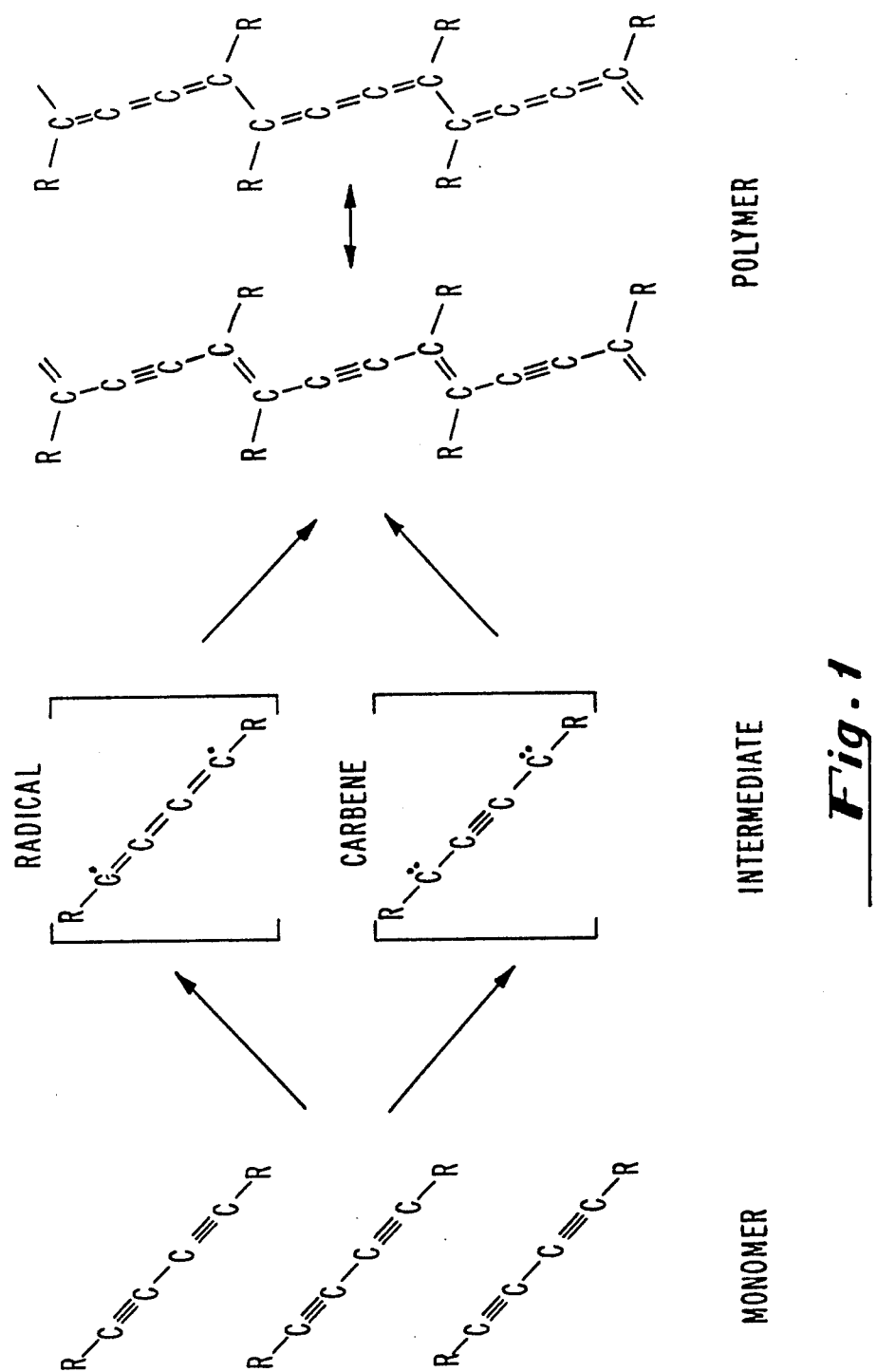
FIG. 1 is a schematic representation of the polymerization of the compositions of the invention according to the processes of the invention whereby a mechanism is postulated. The regularity of assemblages of monomer and the resulting polymer is shown.
Figure 2:
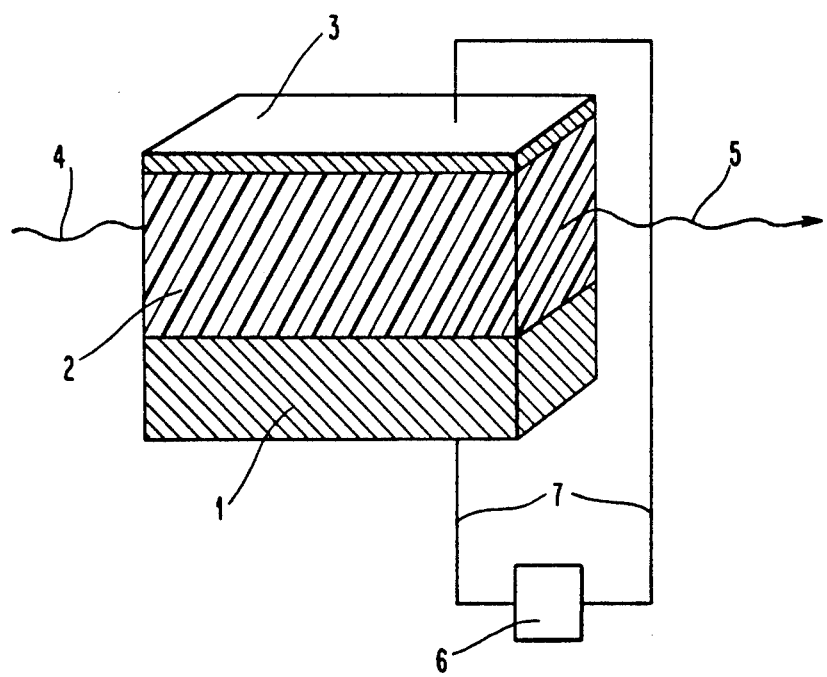
FIG. 2 is a schematic representation of an electro-optic or similar device. 1 is a dielectric or other substrate or composite substrate while 2 is a polymer comprising the material of the invention. In this embodiment are shown a conductor superstrate 3, control means 6, and contacts 7 attached to dielectric or substrate 1 and conductive layer or superstrate 3. This arrangement allows input light signal 4 to be operated upon by by virtue of a changing field within polymer 2 generated by control means 6. Such altered or "operated" output is shown by 5.
Figure 3:
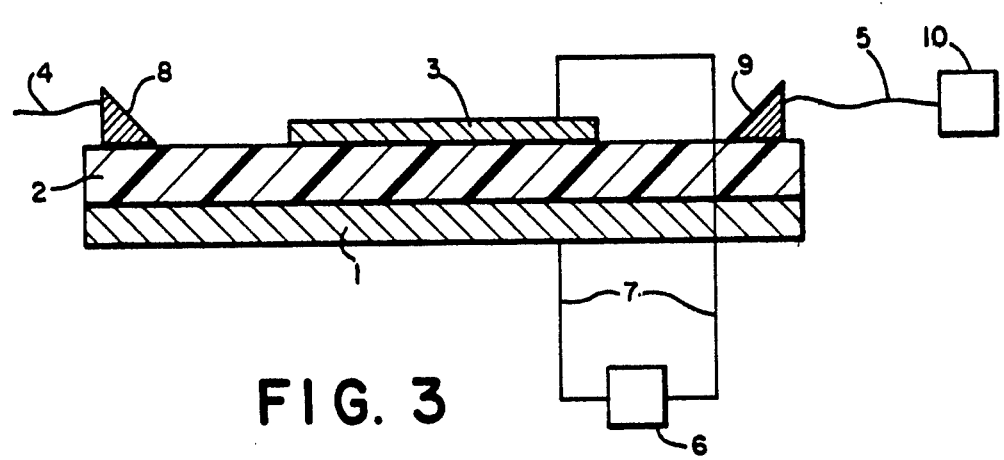
FIG. 3 is a schematic representation of an electro-optic or other device as in FIG. 2 which may be employed to modulate, polarize, frequently select, amplify, or frequency-modify light transmitted therethrough. The article depicted in FIG. 3 may also be employed as an optical logic element. Input signal 4 enters polymer 2 via input coupling means 8. Following transmission of the signal 4 through polymer 2 in the manner described in connection with foregoing FIG. 2, output signal 5 exits the polymer 2 via output coupling means 9. Detector means 10 is oriented in such a fashion as to detect and evaluate the nature and quality of output signal 5.
Figure 4:
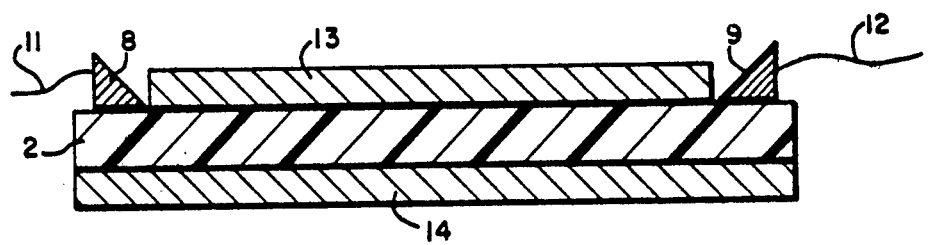
FIG. 4 depicts an optical waveguide in accordance with certain embodiments of the present invention. The polymer of this invention, 2 is interspersed between boundary layers 13 and 14 having indicies of refraction lower than diacetylenic material 2. Input signal 11 transits the waveguide via diacetylenic layer 2 to exit as output signal 12. According to an optional, but preferred embodiment, input coupling means 8, and output coupling means, 9 may also be employed in connection with this embodiment.

Briefly stated, the compositions useful in the practice of the processes of the invention comprise non-linear optical and other materials comprising one or more members of the class of chemical compounds known as diacetylenes. Diacetylenes may be seen to possess at least two carbon-carbon triple bonds (acetylenic bonds) at least two of which triple bonds are in conjugation one with another, i.e. exist in a 1-3 relationship as is illustrated:

$$R_1-C\equiv C-C\equiv C-R_2 \qquad \text{I.}$$
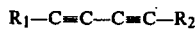

As is known to those skilled in the art, an acetylenic bond possesses a generally linear geometry. It follows that diacetylenes possess a generally linear arrangement of six atoms, the four carbon atoms participating in the diacetylenic "backbone" and each of the two atoms bonded to either end of that backbone. In addition, it is apparent that the diacetylenic structure is rich with electron density. These electronic and geometric properties possessed by the genus of diacetylenes are believed to contribute to the unique suitability of such compounds for inclusion in electro-optic and other compositions as taught by this invention.

Diacetylenes which are suitable for use in one or more embodiments of this invention conform to the general formula:

$$R_1-C\equiv C-C\equiv C-R_2 \qquad \text{I}$$
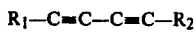

where $R_1$ and $R_2$ may be the same or different and may comprise alkyl, aryl, alkaryl, or aralkyl groups having from one to about 50 carbon atoms. $R_1$ and $R_2$ may in addition, have heteroatomic substitutions or unsaturations. Thus, $R_1$ or $R_2$ may include one or more alkyl, haloalkyl, ester, alcohol, phenol, amine, nitro, amide, halogen, sulfonyl, sulfoxyl, sulfinyl, silyl, siloxyl, phosphoro, phosphato, keto, aldehyde, or other moieties. In addition, metal modifications of any of the foregoing may be included such as, for example, acid or phenolate salt. In addition $R_1$ or $R_2$ or both may be ester, acid, alcohol, phenol, amine, amide, nitro, halogen, sulfonyl, sulfoxyl, silyl, siloxyl, phosphoro, phosphato, keto, aldehydo or a metal salt or phenolate. In short, it is contemplated that any diacetylene may be suitable for use in the practice of one or more of the embodiments of the invention with the exception of those diacetylenes wherein $R_1$ or $R_2$ or both are hydrogen. The latter compositions are not suitable due to the fact that they are, in general, explosive. It is to be understood that the species referred to in this description of the invention may be either straight chain, cyclic, aromatic, or branched. It should also be understood that reference to the compositions of this invention as being diacetylenes does not foreclose the presence of additional acetylenic bonds therein. Thus, compositions having 3, 4, or more acetylenic bonds are foreseen as long as at least two or more of such bonds are in conjugation one with another. Furthermore, additional sites of unsaturation may be present such as carbon-carbon, carbon-oxygen, carbon-nitrogen, or other double or triple bonds, aromatic or heteroaromatic species. Substitution with halogens, hydroxyls, amines, nitros, thiols, silyls, siloxyls, phosphates, sulfates, sulfonates, or other functionalities is also useful.

For the practice of certain embodiments of the invention, diacetylenes may preferably possess the general formula:

$$R_3-C\equiv C-C\equiv C-R_4 \qquad \text{II.}$$

wherein $R_3$ is a hydrophobic chemical moiety and $R_4$ is a hydrophilic chemical moiety. Those skilled in the art will recognize that "hydrophobic" is a term descriptive of chemical moieties or residues which are, in general, unattracted to water or electrically charged species. Thus, hydrocarbon structures which are unsubstituted or sparingly substituted with heteroatomic functionalities are considered hydrophobic. In contrast, a "hydrophilic" moiety species possess one or more acid, ester, alcohol, amino, thiol, or similar heteroatomic substitutents while hydrophobic species are characterized by a substantial lack thereof. Of special utility in the practice of the invention are diacetylenes of formula (II) wherein the substituent $R_3$ comprises a hydrocarbon moiety having from one to about 30 and preferably from 2 to about 20 carbon atoms and wherein $R_4$ may be represented by the formula:

$$-R_5-(A)_n \qquad \text{III.}$$

where $R_5$ is a hydrocarbon having from one to about 50 and preferably from one to about 30 carbon atoms; n is an integer from one to about 10 and preferably one to three; and A is a member of the group consisting of $R_6$, halogen, COOH, $COOR_6$ $CONH_2$ $CONHR_6$, $NO_2OH$, SH, $NH_2$, $NHR_6$, $N(R_6)_2$, silyl, siloxyl, sulfate, sulfinate, phosphate and others where $R_6$ is a hydrocarbon having from one to about 8 carbon atoms. Certain perferred forms of the composition include styryl moieties in the hydrocarbon portion of $R_3$ or include other polymerizable unsaturations such as, for example, dienyl, vinyl or acryryl species.

Certain embodiments of the invention may usefully employ compositions of the formula:

$$R_3-C\equiv C-C\equiv C-R_3 \qquad \text{IV.}$$
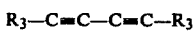

or $$R_4-C\equiv C-C\equiv C-R_4 \qquad \text{V.}$$

where $R_3$ and $R_4$ have any of the identities attributed to them above.

Additional embodiments of the invention may profitably employ diacetylenes of formula (I) where $R_1$ or $R_2$ or both have the formula:

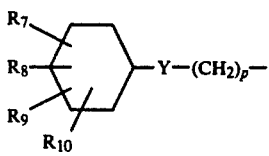 VI.

wherein p is an integer from 0 to about 20 and preferably from one to about 6; Y is O, NH, S, SO$_2$, SO$_3$, SiO$_2$, PO$_3$, PO$_4$, CH$_2$, amido, acetyl, acetoxy, acrylyl, methacrylyl, or styryl, and R$_7$ through R$_{10}$ may be the same or different and may be H, NO$_2$, NH$_2$, monohalomethyl, dihalomethyl, trihalomethyl, halogen, alkyl, perhaloalkyl, alkenyl, or aryl having from one to about 6 carbon atoms; SO$_2$, SO$_3$, PO$_3$, PO$_4$, siloxyl, silyl, etc. In certain preferred compositions, ethylenic groups are included to result in styryl diacetylenic formulations.

In certain preferred compositions, centers of chirality or other forms of asymmetry may be present in the molecular structures and optically active materials may be utilized for certain embodiments. Thus, materials may be utilized such as, for example, those of formula (I) wherein R$_1$ or R$_2$ or both have the formula:

$$-(CH_2)_q-R_{11} \qquad \text{VII.}$$

where q is an integer from 0 to about 20 and R$_{11}$ is a species having a chiral or optically active center. While it is to be understood that any substituent having an optical center is contemplated for use herein, several exemplary embodiments may be represented by the formulas:

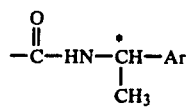 VIII.

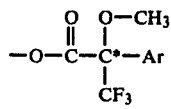 IX.

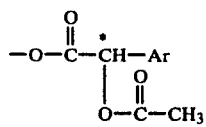 X.

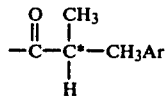 XI.

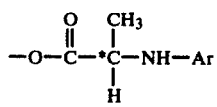 XII.

wherein an asterisk indicates an optical center and Ar is an aryl group. For example, Ar may be represented by either of the formulas:

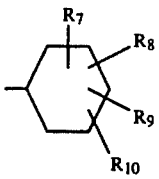 XIII a or

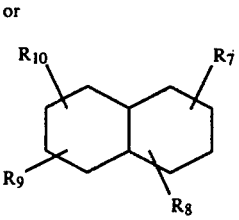 XIII b where R$_7$–R$_{10}$ have the meanings ascribed to them in connection with FIG. VI. In similar fashion, chiral amino acid or other optically active residues may be included in the diacetylenic compositions of the invention.

As will be more fully set forth below, employment of diacetylenes having one or more chiral centers finds preferred usage in systems requiring noncentrosymmetry such as nonlinear optical, piezo- and pyroelectric systems. It should be appreciated that molecules having chirality are, in general, difficult to synthesize and isolate. Thus it should be understood that absent a compelling reason for the synthesis of chiral species, such synthesis is generally avoided in the design of organic synthetic schemes. Understanding of the physical and physiochemical basis for nonlinear optics as reflected in the *Physical Review* article by the inventor, led to an appreciation of the desirability of incorporating chirality in diacetylenic systems for use in the fabrication of nonlinear optical, piezo- and pyroelectric materials. Accordingly, it is believed that the inventor is the first to synthesize diacetylenes having a chiral center.

It should be apparent from the foregoing that while certain diacetylenes are prefered for certain embodiments, no limitation is intended or is to be implied with respect to the diacetylenes suitable for the practice of one or more embodiments of this invention. All compositions which include one or more chemical species having at least two acetylenic bonds, at least two of which are in conjugation one with another are suitable.

Exemplary syntheses of diacetylenes are presented in "Synthesis of N-(nitrophenyl)amine Substituted Diacetylene Monomers" Garito et al, *Makromolecular Chemie (in press)*; "Synthesis of Chiral Diacetylene Polymers", Garito et al, *Makromolecular Chemie* (vol. 180 p. 2975, 1979); "The Chemistry of Diacetylenes", (Wiley, 1974), M. F. Shostakovskii et al; "Synthesis of Nitrophenoxymethyl Substituted Diacetylene Monomers", Kalyanaraman, Garito et al, *Makromolecular Chemie*, vol. 180, June 1979; "Solid State Synthesis and Properties of the Polydiacetylenes", Baughman et al, *Annals of NY Academy of Science*, vol. 313 (1978); "Polymerization of Diacetylene Carbonic Acid Monolayers at the Gas-Water Interface", Day et al, *J. Polymer Sciences, Polymer Letters ed.* vol. 16, p. 205 (1978); and U.S. Pat. No. 3,923,622 issued to Baughman et al.

As a class, diacetylenes exhibit uniquely regular structures in thin films, multi-layer films, and polymers formed therefrom. In thin films formed on substrates, diacetylenes assume a regular orientation. This phenomenon which is illustrated in FIG. 1 is known. See "Kinetics of Thermal Polymerization in the Solid State 2,4-Hexadiyne-1,6-Diol-Bis(p-Toluene Sulfonate)", Garito et al, *J. Polymer Sci.* 16, 335-338(1978); "Kinetics of Solid State Polymerization of 2,4-Hexadiyne-1,6-Diol-Bis(p-Toluene Sulfonate)", Garito et al, *Molecular Metals,* Hatfield ed. (Plenum, 1979); Wegner "Recent Progress in the Chemistry and Physics of Poly (diacetylenes)", *Molecular Metals,* W. E. Hatfield ed. Plenum (1979). Additional reports are contained in *Journal of Polymer Science, Polymer Chemistry ed.,* vol. 17. pp. 1631-1644 (1979) "Polymerization of Diacetylenes in Multi-Layers" by Wegner et al; and *Macromolecular Chemistry,* vol. 179, pp. 1639-1642 (1978) "The Quantum Yield of the Topochemical Photopolymerization of Diacetylenes in Multi-Layers" by Wegner et al; "Solid-State Polymerization of a Nitrophenoxy Disubstituted Diacetylene", Garito, et al. *Makromolecular Chemie* (in press). Reference is specifically made to these reviews and to the references cited therein. Wegner reports on the chemistry, synthesis, structure, orientation and polymerization of diacetylenes and poly(diacetylenes) and describes the multi-layer behavior of certain species thereof. The regular orientation in a thin film has been reported to be in a "herringbone" array. The arrays may be quite large and may, it is believed, extend over the entire area of the film. Wegner has observed large domains thought to be formed of areas of regular orientation. It is possible to form single domain films which can polymerize into single domain polymers.

The chemical molecular structure of such polymers, while not entirely clear, is subject to interpretation. As shown in FIG. 1, polymers of diacetylenes are believed to possess triple and double bonds in a 1 ∝ 3 relationship in the subunits of the polymer. It will be understood by those skilled in the art that the two "resonance structures" indicated for the polymer represents the fact that, with poly(diacetylenes) as with most organic molecules, structural description in terms of bond order i.e., triple, double etc. is less than precise. Thus, with the understanding that the polymers possess bond characteristics which are not fully representable as any one single structure, such polymers will be described as having a repeating subunit wherein four carbon atoms are aligned in a generally linear configuration.

Thus, the polymers produced according to the practice of this invention may be alternatively described as (1) being substantially regular in orientation, at least within any polymer domain; (2) having an acetylenic bond in the subunit structure thereof, or (3) possessing subunits which have four carbon atoms in a generally liner configuration.

According to a preferred practice of the invention, substrates are coated with diacetylenic compositions. These coatings may be elaborated in such a fashion that high regularity and periodicity of structure results such as is illustrated in FIG. 1. Such coating of substrates with diacetylenic compositions is preferably accomplished by the Langmuir-Blodgett technique. This technique, which is well known to those skilled in the art, causes a thin film of diacetylene to be deposited upon the surface of a fluid. The surface layer is then compressed to minimize the surface area occupied by the diacetylene so as to effect a closest packing arrangement thereof. This closely packed and arrayed diacetylenic composition is then transferred to a substrate by dipping. The use of diacetylenes having hydrophobic and hydrophilic substituents on either end thereof facilitates the use of the technique. Multi-layers may be built up sequentially by this technique. These multi-layers may be uniform in composition or may be dissimilar. They may number from two to several hundreds and may, thus, comprise thin or thick films.

Alternative means of placing diacetylenes on substrates may be utilized as well. Thus, the "whirling" or spinning technique as described in the DeForest reference, roller coating as is currently practiced in the art, or even dipping may be employed so to apply the diacetylenic species to the substrate. Coating by vapor deposition may also be employed.

The regularity which may be accomplished in the establishment of films or coatings of diacetylenes according to a preferred practice of this invention may carry over to the polymers formed therefrom. In FIG. 1, the geometry of the arrays of monomeric diacetylenes which may be established is very nearly the same as the geometry of the subsequently formed polymers. In an exemplary case, the difference in orientation geometry is less than 5 degrees. This fact coupled with the nearly ideal orientation of polymerizable moieties with regard to each other and the concomitantly excellent polymerization yields efficiently contribute to the overall regularity in the polymerized species which are thus formed.

As will be readily apparent to those skilled in the art, the extreme regularity which is possessed by those polymers extends not only to geometric and steric regularity, but also to electronic and compositional regularity as well. Thus, polymers formed from monomers with a given functionality or feature present therein will exhibit this functionality or feature on a substantially periodic basis throughout the polymer. Similarly, due to this regularity, polymer films on coatings may be formed which have uniform dimensions, especially uniform thicknesses. A further manifestation of the unique structure of these polymers is the electronic regularity occuring therein. Thus the alternating double and triple bonds which (according to one viewpoint) occurs in the "backbones" of the polymers combines with the regularity of the backbones inter se, it is believed, to result in a uniquely regular pi electronic density associated with the polymer. All of these factors are thought to contribute to the extreme suitability of the polymers of this invention for the electronic, electro-optic and other uses taught hereby.

The materials of this invention may be employed otherwise than in thin films to result in electronic, electro-optic and other devices. Thus single crystals of the diacetylenic materials disclosed herein may be grown by any of the techniques known to those skilled in the art; those crystals may be designed to exhibit many of the properties shown by thin film devices. Thus single crystals having extremely high electrooptic, electroacoustic, SHG, peizoelectric, and pyroelectric effects may be formulated.

The compositions useful in the practice of the invention may include species in addition to the aforedescribed diacetylenes. Thus, additional polymerizable materials may be added as may catalysts, sensitizers, pigments, dyes, fillers and dopants. Additionally, organic or inorganic materials may be included to alter the electrical properties of the compositions. The additional polymerizable materials which may be included may encompass any of the wide variety of polymerizable species known to those skilled in the art. Olefinics such as vinyl, styryl, acrylic, dienyl, etc. are preferred.

Of these, dienyl and acrylic species are most preferred. Dimers of nitroso compounds may also be included to modify the polymerization behavior. The composition may, optionally, contain a sensitizer or catalyst to improve the photochemical interaction between the monomeric compositions and incident radiation. Such sensitizers are well known in the art and include, for example, acetophenone, acyloin derivatives, benzophenone, dyes such as indigo derivatives and many other species. The sensitizers may be included in amounts up to about 5% by weight of composition and preferably between about 1% and about 3%. In an alternative embodiment, one or more layers of diacetylenic composition may be "sandwiched" with layers of sensitizer-containing formulation to give good results.

Other compositions may include polymerizable sites in the diacetylenic species in addition to the diacetylenic bonds themselves. Thus, diacetylenic compounds having acrylic, styryl, vinyl or other polymerizable functionalities may be used to good result. In such a case, the polymerization of such additional polymerizable structures may be accomplished concomitantly with or subsequent to the polymerization of the "backbone" diacetylenes. In cases where multiple single layers of oriented diacetylenes are laid down upon a substrate, it may be seen that polymerization of the "backbone" may occur almost exclusively within one layer. The presence of other polymerization or crosslinking agents may result in interlayer linking to yield useful materials. The inclusion of styrene residues is especially preferred for this purpose.

Polymerization of the layers, coatings, arrays or crystals of the diacetylenes taught hereby may be accomplished in any of the ways which are well known to those skilled in the art. Thus, simple heating, preferably with a radical initiator present in the formulation, or photoinitiation, either with or without a sensitizer is suitable. The latter procedure is preferred due to the ability of those skilled in the art to polymerize selectively those portions of the whole which are desired to be polymerized without substantial polymerization of other areas. In this regard, reference is made to Ser. No. 052,007 of which this application is a continuation in part and to Ser. No. 113,552) which is copending with this application and which has been incorporated herein by reference. This ability facilitates the microfabrication of thin film patterns in ways analogous to those employed in photolithography. Such patterns of polymer which display electronic, electro-optic, waveguide or other properties may be employed in numerous microcircuitry and other applications as will be apparent to those skilled in the art. Macroscopic use is, of course, also forseen and intended hereby.

As has been indicated, electro-optic, electro-acoustic, SHG, and related effects employ diacetylenic materials which are crystallizable into crystals having a noncentrosymmetric unit cell. It is further to be considered that the accomplishment of higher degrees of asymmetry are, in general, rewarded with materials and devices having higher degrees of non-linear optic effect as long as a suitable electronic structure is maintained. Some of the diacetylenes which exhibit the most pronounced electro-optic and other nonlinear optic effects are those which include one or more chiral centers. Thus diacetylenes according to Formula (I) wherein $R_1$ or $R_2$ or both have the Formula (VII) are preferred. As will be appreciated by those skilled in the art the degree of asymmetry present in a chiral molecule will vary as the substitution pattern on the asymmetric center varies. Especially useful materials have been formulated having two or more chiral centers, either one or both ends of the diacetylenic core. Examples of chiral diacetylenes which are preferred for nonlinear optical uses are represented by the formulas:

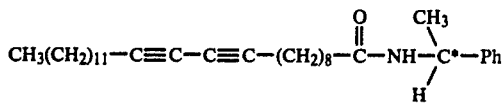

XIV.

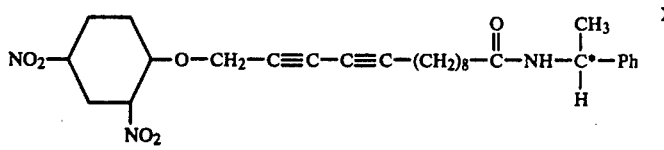

XV.

while a preferred diacetylene having two such groups is represented by the structure:

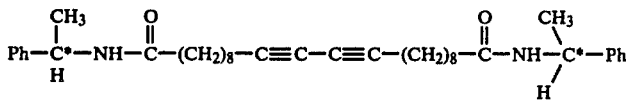

XVI.

These and numerous other chiral diacetylenes which may form crystals having a non-centrosymmetric unit cell for use as nonlinear optical, piezo-, and pyroelectric materials.

Noncentrosymmetric diacetylenic molecules which do not have chirality are also suitable for use in one or more nonlinear optical or related systems. Thus, any diacetylene species which has no center of inversion symmetry may be employed. One such preferred material for electro-optic and SHG purposes is represented by the formula:

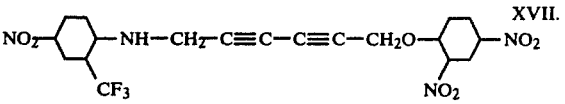

XVII.

Such material and its analogs have been found to be high asymmetric on both the molecular and unit cell level and have demonstrated high electro-optic coefficients. Other asymmetric diacetylenes are similarly useful.

Many of the diacetylenes which may be employed in non-linear optic systems, i.e. those which are crystallizable into crystals having non-centrosymmetric unit cells, may evidence second harmonic generation which is phase matchable. Phase matchability, which has been explained above, makes these materials extremely well suited for use as SHG media. While at the present time it has not been possible to predict which of the diacetylenes will exhibit phase matchability, routine experimentation will identify members of the class. The suitability of the diacetylenes of this invention for use as phase matchable second harmonic generating media is easily ascertained. Diacetylenes which are to be tested are powdered and exposed to laser light. The second harmonic generation shown by the diacetylene species is compared to an internal standard, lithium iodate, and qualitatively evaluated. This procedure, which is well known to those skilled in the art discloses that many of the diacetylenes are superior to the standard. Further exemplary species among these are:

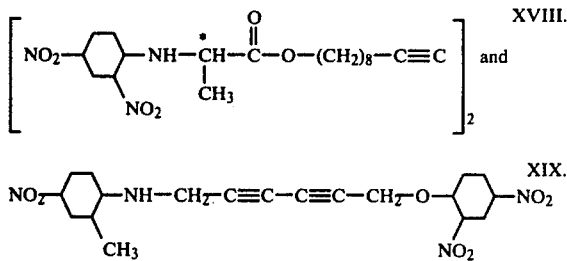

Numerous others are, of course, also suitable. Those molecules identified as XIV to XVII are believed to exhibit phase matchability and, accordingly, represent preferred material for SHG use. It is expected that large numbers of additional diacetylenes will also be so identified.

As has been explained, those materials which are useful for piezoelectric and pyroelectric applications share symmetry requirements with nonlinear optical systems and, hence, must possess no center of inversion symmetry. It will be understood that appreciable piezo- and pyroelectric effects can be exhibited by those diacetylenes having noncentrosymmetry without regard to the electronic nature of the species. Such materials therefore encompass all of those diacetylenes which are noncentrosymmetric on a crystalline unit cell basis, and all such diacetylenes may be predicted to exhibit piezo-, or pyroelectric activity.

For use as waveguides diacetylenes according to this invention are not constrained in terms of symmetry. For waveguiding purposes it is necessary only that the diacetylene have a regular physical structure and uniform index of refraction. According to preferred practice, layers of diacetylenic material may be built up into waveguides or other structures having definite dimensions by use of the Langmuir-Blodgett method and other techniques. Those skilled in the art will appreciate that the index of refraction of a diacetylenic composition will vary depending upon the diacetylene moieties chosen for inclusion therein. Thus, layers of uniform thickness of differing diacetylenic species may be deposited upon a substrate and, preferably, subsequently, polymerized to result in planar waveguides of high efficiency. By virtue of the extreme regularity which is present in the diacetylene monomers and polymers as taught herein, waveguides having very low loss rates are possible. Of course, discetylene layers may be bounded by nondiacetylne layers to result in planor waveguides as long as the boundry layers have a lower index of rejection than the diacetylene layer.

Those skilled in the art will readily recognize that the various embodiment of the present invention may be combined to yield devices of great flexibility and use. The waveguiding properties of the diacetylenes may be combined with the nonlinear optical properties so that a guided light wave can be operated upon electro-optically or the like. In a similar fashion, piezoelectric properties may be designed into a waveguide so that, for example, a physical motion may be coupled to a propagated light wave. Indeed, large arrays of nonlinear optical, piezoelectric, semiconductor and other devices may be formed within a waveguiding system so as to result in assemblies of devices of diverse character and use. It will be apparent to one skilled in the art that, in such fashion, miniaturized electro-optic logic networks may conveniently be established. Such materials are useful on a macroscopic scale as well. Thus piezoelectric or pyroelectric arrays may be had in sheet or film form which may have dimensions on the order of meters. It will be apparent that numerous other macroscopic uses are also possible for such systems.

For certain applications, it is highly beneficial to provide a strong adherence of the coatings to the underlying substrate. It has been found to be possible to bond such coatings to substrates covalently utilizing certain techniques. Thus, hydroxyl or other functional groups commonly found on the surfaces of substrates may be utilized to consummate silyl or siloxyl linkages with a suitably silicon substituted diacetylenic species. See E. P. Plueddemann "Mechanism of Adhesion Through Silane Coupling Agents" in *Composite Materials*, Brautman; Krock eds, vol. 6, ch. 6, Academy Press (1974). Other means of covalently bonding film to substrates or of film precursor species to substrates will readily occur to those skilled in the art. Thus, it is desirable to coat the substrate with a composition which may form covalent linkages with such substrate and which may also form covalent linkages with the diacetylenic species which comprise the nonlinear optical or other layers. While any composition which will form covalent bonding may be employed, preferred species for accomplishing such covalent bonding may be represented by the formula:

(HO-R$_{12}$)$_3$-Si(R$_{13}$)Z         XX.

where the R$_{12}$ groups may be the same or different and are hydrocarbyl groups having from one to about six carbon atoms, where R$_{13}$ is a hydrocarbyl group having from one to about six carbon atoms, and Z is any substituent which may covalently bond with the diacetylenic specie of choice. Preferably, Z is an amine, and is used to form an amide linkage with a carboxyl group on the diacetylene, but any suitable substitutent may be employed. One such exemplary composition is 3-aminopropyltriethoxysilane which is described by Formula XX when R$_{12}$ is ethyl, R$_{13}$ is propyl and Z is amino. It will be understood that covalent bonds other than the siloxyl and amide bonds described above may be satisfactorily employed in the practice of the invention.

The fabrication of articles employing the novel materials and processes of this invention is not complex. Those skilled in the art will recognize that single crystals of suitable diacetylenic species may be grown employing an appropriate solvent recrystallization system.

Thus, for example either of the materials XVII or XIX may be recrystallized from a polar solvent such as nitromethane in manners well known to those skilled in the art to yield satisfactorily large single crystals. To employ such single crystals in the generation of second harmonics it is necessary only to pass intense laser light through such crystals. The generation of second harmonics will occur spontaneously within the crystals and a mixture of fundamental and doubled frequencies will emerge. A conventional filter designed so as to filter out the fundamental frequencies is helpful in isolating and identifying the second harmonic. It will be appreciated by those skilled in the art and upon perusal of the Kaminow work cited previously, that such second haromnic may be generated over a spectrum of laser frequencies with but small changes in efficiency. It is, in general, necessary only that the medium be transparent to both the fundamental frequency and its second harmonic.

The electro-optic and other nonlinear optical effects may be evidenced by single crystals formed of the diacetylenic materials taught by the present invention. Thus, a single crystal of, for example, either of the material XVII or XIX may be fitted with electrical contacts on appropriately located (generally parallel) crystal faces or otherwise adapted with means for generation of an electric field within such crystal. Passage of intense laser light through the crystal at a time when the electric field is being modulated by a suitable control means will result in a modulation of the light signal. It will be appreciated that the crystal must be transparent to both the incident and exit light frequencies. Those skilled in the art will further appreciate that other nonlinear optical phenomena may be accomplished in a similar way employing single crystals of suitable diacetylenes. All of these uses may also be accomplished through the employment of films of diacetylenes either polymerized or not.

The use of single crystals for piezoelectric and pyroelectric devices has long been known in the art; such may be accomplished with diacetylenes as well. Thus, it is necessary only to grow a crystal of a suitable diacetylene such as, for example, XVII or XIX and to fit the crystal with a means for the establishment of an electrical potential across opposite faces of such crystal to construct a piezoelectric or pyroelectric device from the materials and processes of the present invention.

To formulate waveguides from the diacetylenes of the present invention, a thin film of diacetylenic material is elaborated on a substrate, which substrate has an index of refraction less than the index of refraction of the film. Additionally, a superstrate, also having an index of refraction less than the index of refraction of the film, is placed on top of the film. Thus, it may be seen that there is a layer of diacetylenic material bounded by two other layers having indices of refraction less than the index of the diacetylenic layer. For most applications, the diacetylene may preferably be polymerized to yield waveguiding structures of high physical integrity. A preferred form of such waveguide employs covalently bonding species such as the aforementioned silane bonding species between the film and either or both of the substrate and superstrate. Since the siloxanes which result from this process have indices of refraction which are, in general, less than the indices of refraction of the polydiacetylenes, the waveguiding requirements are maintained. Additionally, it will be readily appreciated that such covalent bonding adds materially to the coherency and strength of the aggregate waveguide. In the alternative, it is possible to build up plurality of layers of diacetylenes and/or diacetylenes modified with other species to result in suitable waveguiding combinations. It will further be appreciated that such waveguides are most useful when the diacetylenes have been polymerized into polydiacetylenes, thus, to evidence the desired coherency and strength. Those skilled in the art will recognize that for employment of waveguides according to the present invention it will be necessary to couple light into and out of the guide. For this function are known many coupling means such as prism couplers, grating couplers, and direct impingement devices. As will also be appreciated by those skilled in the art, light waves being propagated by waveguide according to the present invention may be operated upon by electro-optic, SHG, other nonlinear optic, piezoelectric, and other devices which are included in one or more sections or segments of the guide. According to one embodiment, electro-optically functional waveguides formed of the diacetylenes of this invention may be laid down upon a substrate which is semiconducting to yield useful devices.

Waveguides made according to the above general description may be formulated from materials which have electro-optic, SHG, other nonlinear optical, piezoelectric, pyroelectric, or other properties. Thus, a planar waveguide may be also a nonlinear optic device. For such use, it is necessary only that the diacetylenic film comprise a diacetylene which exhibits nonlinear optical or other properties. Thus, a waveguide which is formulated from, for example, the material XIV will not only guide laser light, but will also generate second harmonics or may be fitted with field generation means for electro-optically operating upon such laser light. It will be readily appreciated that complex aggregates of electro-optics, piezoelectric, and other devices may be placed in large waveguiding arrays so as to perform complex integrated systems for operating upon light. Thus, an optic logical device may be so elaborated.

Piezoelectric and pyroelectric devices may also be developed employing thin film structures. Thus, thin film structural aggregates fitted with the appropriate electrodes may be used as piezoelectric and pyroelectric components.

In the elaboration of these thin film devices, the Langmuir-Blodgett film making technique is frequently preferred. Photolithographic processes as described in Serial No. 133,552 are convenient for elaborating arrays of components. Other methods such as spinning, or vapor coating as described hereinbefore may also be used. These latter procedures are especially useful for the elaboration of thin film waveguides.

The following examples are intended to illustrate certain preferred compositions and processes according to the instant invention. Copending application Serial No. 113,552 which specification has been incorporated herein by reference, presents other examples which are pertinent to the practice of one or more embodiments of the present invention.

EXAMPLE 1

Synthesis of Diacetylene alkyl-acid monomers

Pentacosa-10,12-diynoic acid

Diacetylene alkyl-acid monomers for use in mono- and multilayer preparations were synthesized by the Chodkiewicz coupling procedure using bromoacetylenes prepared following Strauss. See Chodkiewicz *W*.

Ann. Chem. (Paris) 2, 853 (1957) and Strauss, et al, Ber. 63B, 1868 (1930). For example, 1-bromo undecyn-10-oic acid was coupled to tetradecyne to form pentacosa-10,12-diynoic acid. 50 mmol of tetradecyne dissolved in 5 ml ethanol was added with stirring to a 50 ml ethanol solution of 100 mmol hydroxylamine hydrochloride, 10 mmol Cu Cl and 200 m.mole of ethylamine forming a yellow solution. The stirred solution was cooled to 1° C. and 50 m.moles of 1-bromo-undecyn-10-oic acid dissolved in 60 ml ethanol was added dropwise over 30 minutes while the temperature was maintained at 15°-20° C. After the addition was complete the reaction mixture was stirred for 3 hours at 15°-20° C. The mixture was then acidfied to pH 1 and extracted twice with 100 ml ethyl acetate. The organic layer was separated, dried over magnesium sulfate, filtered through fluorosil and evaporated to give a colorless, viscous oil. The oil was taken up in methanol-petroleum ether and the solution was filtered. Upon cooling of the filtrate, pentacosa-10,12-diynoic acid crystallized as colorless platelets (m.p. 59°-60° C.). The platelets become an intense blue upon standing in laboratory light for a short time.

EXAMPLE 2

The apparatus used for multilayer preparation consists of a Langmuir trough made of Teflon with dimensions of 12.2×30 cm area and 2 cm deep. The surface pressure is applied by a movable Teflon barrier connected to a motor driven screw gear. A Wilhelmy balance is used continuously to measure the surface pressure. The solid substrate is connected to a vibration-free solid rod and move in and out of the trough using a reversibly geared motor at speeds of 1-3 cm/hr.

A $4 \times 10^{-3}$ M solution of pentacosa-10,12-diynoic acid in n-hexane was spread on a $1 \times 10^{-3}$ M solution of cadmium chloride in water. The pH of the $CdCl_2$ solution was previously adjusted to 6.1 using sodium bicarbonate. Successive layers were deposited on the solid substrates, at a constant surface pressure of 15 dyne per cm with a dipping speed of 0.5 mm/sec. Surface pressure area curves show that near 23° C. and a surface pressure of about 15 dyne/cm, a monomer molecule occupies $20A^2$; Y type deposition of the layers was observed.

EXAMPLE 3

Preparation of a covalently bound diacetylene on a silicon surface.

Silicon plates with an oxide layer 100μ thick were immersed in concentrated nitric acid for two hours. After rinsing with water, the water contact angle (αw) was determined to be 44° C. After thorough drying, the plates were treated with vapors of 3-aminopropyl triethoxysilane The substrate was placed above a boiling solution of 2 ml of the silane in 100 ml dry p-xylene under nitrogen for 16 hours. The substrate was bathed in the vapor, the vapor condensing 5 cm above the substrate. The substrate was rinsed in absolute ethanol and water, αw was determined to be 45° C. The silanated substrate was immersed in a solution of 22 mg (0.06 mmol) of 10,12-pentacosadiynoic acid in 10 ml anhydrous pyridine. A solution of 14 mg (0.07 mmol) of N,N-dicyclohexylcarbodiimide in 1 ml pyridine was added. The wafers were treated for 16 hours at room temperature under nitrogen. The substrate was rinsed with pyridine, ethanol, boiling pyridine, and boiling ethanol and dried. The αw was determined to be 78° C.

EXAMPLE 4

Preparation of N-d(+)(α-methylbenzyl)-10,12-pentacosadiynamide

To a solution of 510 mg (1.36 mmol) of 10,12-pentacosadiynoic acid in 10 ml tetrahydrofuran was added 138 mg (1.36 mmol) of triethylamine. The resulting cloudy solution was cooled to 0° C. and 129 mg (1.36 mmol) of methyl chloroformate was added dropwise over 1 min. A white solid formed immediately upon addition. The mixture was stirred 1 hour at 0° C., then 165mg (1.36 mmol) of d(+)-α-methylbenzylamine was added and the mixture was heated at reflux for one hour. Gas evolution was evident within five minutes of addition, and ceased after 15 minutes. The mixture was cooled to room temperature and filtered. The filtrate was washed with 10 ml portions of 1 M HCl, water, and saturated aqueous potassium bicarbonate solution, and dried over ($MgSO_4$). Evaporation yielded 540 mg (83% crude yield) of a white solid. Recrystallization from ether-petroleum ether gave white crystals, m.p. 65.5°-66.5° C. IR film: 1470, 1545, 1640, 1860, 1925, and 3310 cm$^{-1}$. $[\alpha]D^{31}(CHCl_3)=44°$ C.

EXAMPLE 5

Preparation of N,N'-bis-(α-methylbenzyl)-10,12-docasadiyndiamide

To a solution of 725 mg (2.00 mmol) of 10,12-docasadiyndioic acid in 50 ml THF was added 405 mg (4.00 mmol) of triethylamine. The solution was cooled to 0° C. and 378 mg (4.00 mmol) of methyl chloroformate was added dropwise over one minute. The resulting white mixture was stirred one hour at 0° C., and 485 mg (4.00 mmol) of d(+)-α-methylbenzylamine was added. The reaction mixture was heated at reflux for one hour (gas evolution began immediately upon amine addition and ceased after 20 minutes). The mixture was cooled to room temperature and filtered. The filtrate was washed with 25 ml portions of 1 M HCl, water, and saturated aqueous sodium bicarbonate solution and dried over ($MgSO_4$). Evaporation yielded 842 mg (74% crude yield) of a white solid, which polymerized rapidly upon exposure to UV light. Recrystallizatron from ether-petroleum ether gave 456 mg of white crystals, m.p. 87.5°-89° C.; IR(film): 1530, 1635, 2850, 2920, and 3300 cm$^{-1}$.

EXAMPLE 6

Preparation of 11-bromo-10-undecynoic acid

To a solution of 36.45 g (200 mmol) of 10-undecynoic acid in 200 ml 1 N NaOH at 0° C. was added a solution of alkaline sodium hypobromite dropwise over 30 minutes, maintaining the temperature below 5° C. (the hypobromite solution was prepared by the dropwise addition of 35.16 g (220 mmol) of bromine to 55 ml of 20 N NaOH at 0°-5° C.). The mixture was stirred four hours at 0°-5° C., and was then acidified to PH 1 with 9 M $H_2SO_4$. The solution was extracted with three 150 ml portions of ether. The combined extracts were dried ($Na_2SO_4$) and evaporated yielding 50.159 (96% crude) of a pale yellow solid. THis was used without further purification.

Example 7

Preparation of N-(α-methylbenzyl)-11-bromo-10-undecynamide

To a solution of 2.612 g (10 mmol) of 1-bromo-10-undecynoic acid in 100 ml THF was added 1.012 g (10 mmol) of triethylamine. The solution was cooled to 0° C. and 0.945 g (10 mmol) of methyl chloroformate was added dropwise over 3 minutes. The resulting cloudy white mixture was stirred 1 hr. at 0° C., then 1.212 g of d(+)-α-methylbenzylamine was then added. The resulting mixture was heated to reflux 1 hour (gas evaporation began within 5 minutes of addition and ceased after 20 minutes). The mixture was cooled to room temperature and filtered. The filtrate was washed with 50 ml portions of 1 N HCl, water, and saturated aqueous potassium bicarbonate solution and dried over (MgSO$_4$). Evaporation gave 3.217 g (88% crude yield) of a pale yellow solid. IR (film): 1450, 1540, 1640, 2860, 2940, and 3300 cm$^{-1}$.

EXAMPLE 8

Preparation of N-(α-methylbenzyl)-14-hydroxy-10,12-tetradecadiynamide

To a solution of 20 mg (0.10 mmol) of cuprous chloride, 175 mg (2.50 mmol) of hydroxylamine hydrochloride, and 980 mg (21.7 mmol) of 70% aqueous ethylamine in 5 ml water was added 981 mg (17.5 mmol) of propargyl alcohol. The resulting yellow mixture was stirred 5 minutes at ambient temperature, and a solution of 911 mg (2.50 mmol) of N-(α-methylbenzyl)-11-bromo-10-undecynamide in 20 ml DMSO was then added dropwise over 20 minutes. The mixture was stirred 3 hours at ambient temperature (the solution became clear after 1 hour) and then was acidified to pH 1 with concentrated HCl. The solution was extracted with three 75 ml portions of ethyl acetate. The combined organic extracts were washed with two 100 ml portions of water and two 100 ml portions of brine and dried over (MgSO$_4$). Evaporation gave 815 mg of a viscous pale yellow oil. NMR indicated a mixture of approximately 1:1 starting amide and coupled hydroxyamide. The product was purified by column chromatography (silica gel, 60% ether-hexanes as eluent), affording starting amide R$_f$0.45, 80% ether-hexanes) and 220 mg of a colorless oil (R$_f$0.15, 80% ether-hexanes).

EXAMPLE 9

Preparation of N-(α-methylbenzyl-14-(2,4-dinitrophenoxy)-10,12-tetradecadiynamide To a solution of 220 mg (0.65 mmol) of N-(α-methylbenzyl)-14-hydroxy-10,12-tetradecadiynamide in 10 ml DMSO was added 506 mg (5.00 mmol) of triethylamine. To the solution was then added 130 mg (0.70 mmol) of 2,4-dinitrofluorobenzene. The resulting red solution was stirred 16 hours at ambient temperature, and 25 ml of saturated aqueous potassium bicarbonate solution was then added. After stirring 15 minutes, the mixture was poured into 100 ml of water and the resulting solution was extracted with 100 ml portions of ethyl acetate. The combined organic extracts were washed with three 50 ml portions of water and three 50 ml portions of saturated aqueous sodium bicarbonate solution and dried over (MgSO$_4$). Evaporation gave 312 mg of a red oil. NMR indicated no starting alcohol was present.

The product was purified by passing it through silica gel (ether as eluent); crystallization from ether petroleum ether gave white crystals, m.p. 59°-60° C. NMR (CDCl$_3$): 9.42-7.30, m, 8 H aryl H's; 6.00, br s, 1 H, N-H; 5.10, br s 2 H, O—CH$_3$C≡C and m, 1 H, CHCH$_3$; 2.30, m, 4 H, C≡CH$_2$CH$_2$ and —CH$_2$CO—; 1.55, d, J=7 Hz, 3 H, CH$_3$ and 1.70-1.20, m, 12 H, other CH$_2$.

EXAMPLE 10

2,4-Hexadiyn-1,6-diol-bis-(2,4-dinitrophenyl) ether

To a solution of 2,4-hexadiyn-1,6-diol(1.1 g) in acetone (15 ml), K$_2$CO$_3$ (0.5 g) was added. To the stirred solution at room temperature, 2,4-dintrofluorobenzene (3.8 g) was added gradually and the dark red solution stirred overnight at room temperature. It was poured into excess water, the pale yellow solid filtered off, washed with water and dried. Recrystallization from dioxaneethanol gave short, light pink needles, m.p. 210° C., (4.2 g., 95%). IR (KBr): 1592, 1333, 834 (Ar-NO$_2$)cm$^{-1}$.

EXAMPLE 11

N-(2-Propynyl)-2,4-dinitroaniline

To a suspension of potassium carbonate (1.0 g) in acetone (10 ml) was added 2-propyn-1-amine (0.26 g, 473×10$^{-3}$ mole). 2,4-Dinitrofluorobenzene (1.32 g, 7.10×10$^{-3}$ mole) was gradually added with stirring and the reaction mixture was refluxed two hours. After cooling it was poured into excess water and filtered. Recrystallization of the crude solid from ethanol afforded yellow needles; m.p. 151°-152° C. Yield: 0.99 g (95%). IR (KBr): 3367 (NH), 3268 (≡CH), 1618, 1590, 1333 and 1311 cm$^{-1}$ (Ar-NO$_2$).

EXAMPLE 12

N,N'-Bis(2,4-dinitrophenyl)-2,4-hexadiyn-1,6-diamine

To a suspension of Cu(OAc)$_2$.H$_2$0 (1.5 g) in pyridinemethanol (1:1, 10 ml) was added N-(2-propynyl)-2,4-dinitroaniline (1.00 g, 4.52×10$^{-1}$ mole). The reaction mixture was stirred at 50° C. for 30 minutes. The mixture was poured into excess water, and filtered. The crude solid was recrystallized from nitromethane to afford pale green crystals. Yield: 0.86 g (86%). The compound failed to melt at 200° C. but changed from green to bronze color at 120° C. It could be recrystallized from dioxane to give a different crystal form, appearing as orange crystals which turn deep orange at 140° C. IR (KBr): 3380 (NH), 1617, 1592, 1333 and 1312 cm$^{-1}$ (Ar-NO$_2$).

EXAMPLE 13

6-Hydroxy-2,4-hexadiynyl-1-(4-nitro-2-trifluoromethyl)aniline

To a suspension of Cu(OAc)$_2$.H$_2$O (89.6 g, 4.49×10$^{-1}$ mole) in pyridine-methanol (1:1, 500 ml) at 0° C., was added N-(2-propynyl)-4-nitro-2-trifluoromethylaniline (5.01 g, 2.05×10$^{-2}$ mole) and 2-propyn-1-ol (2.76 g, 4.91×10$^{-2}$ mol. Additional 2-propynl1-ol (20.83 g, 3.72×10$^{-1}$ mole) was dissolved in methanol (25 ml) and added dropwise over 6 hours as the reaction was gradually allowed to warm to room temperature. The reaction mixture was stirred for an additional 1 hour and poured into water (3500 ml). Filtration gave a pink solid that was chromatographed on a silica column, eluting with chloroform, to give a pale yellow solid. Recrystallization from toluene-petroleum ether gave 1.96 g, (b 32%) m.p. 142°-144° C. I.R. (KBr): 3480 (NH), 3460 (OH), 1583 (Ar-NO$_2$) and 1307 cm$^{-1}$ (CF$_3$).

EXAMPLE 14

Synthesis of:
6-(2,4-dinitrophenoxy)-2,4-hexadiynyl-1-
-(4-nitro-2-trifluoromethyl)aniline 6-hydroxy-2,4-hexadiynyl-1-(4-nitro-2-trifluoromethyl)aniline (1.00 g, 3.36×10$^{-3}$ mole), K$_2$CO$_3$(2 g), triethylamine (1 ml), and dinitrofluorobenzene (3.00 g, 1.61×10$^{-1}$ mole) were refluxed in acetone (30 ml) for 4 hours and stirred at room temperature for 12 hours. The reaction mixture was poured into water (300 ml) and extracted with ethyl acetate. The ethyl acetate solution was washed with saturated aqueous sodium bicarbonate solution, then water, and dried over magnesium sulfate, filtered and evaporated. The residue was chromatographed on a silica column, eluting with chloroform to give crude product. This was then rechromatographed on a silica column eluting with toluene to give product as a pure solid (one spot by TLC on silica with 1:3 ethyl acetate-chloroform). Recrystallization from toluene-petroleum ether (hot) gave a pale yellow solid (1.25 g, 80%) m.p. 184°-185° C. (with decomposition). $^1$H NMR (acetone-d$_6$-DMSO-D$_6$):=4.35 (d:2H, J=6 Hz), 5.18 (s:2 H), 6.50-8.75 (M:7 H).

EXAMPLE 15

6-Chloro-2,4-hexadiynyl-1-(2,4-dinitro)analine

A solution of 6-hydroxy-2,4-hexadiynyl-1-(2,4-dinitro) aniline (0.99 g, 3.60×10$^{-1}$ mole) in dry pyridine (5 ml) was cooled in an ice bath and a solution of p-toluene sulfonyl chloride (3.34 g, 1.75×10$^{-2}$ mole) in pyridine (5 ml) was added dropwise. The reaction mixture was kept at 0° C. for 5 hours. At the end of this time, the reaction mixture was poured into water (300 ml), acidified with aqueous HCl (30%) and extracted with chloroform. The chloroform layer was washed with aqueous saturated sodium bicarbonate then dried over sodium sulfate, filtered and evaporated. The residue was chromatographed on a silica column, eluting with chloroform and recrystallized from benzene-petroleum ether to give 0.33 g, (31%) as pale yellow crystals, m.p. 122°-123° C. I.R. (neat): 3345 (NH, 1605 and 1587 cm$^{-1}$ (Ar-NO$_2$).

EXAMPLE 16

6-(4-Nitrobenzoyl)-2,4-hexadiynyl-1-(4-nitro-2-trifluoromethyl)aniline

To a solution of 6-hydroxy-2,4-hexadiynyl-1-(4-nitro-2-trifluoromethyl)aniline (0.14 g, 4.70×10$^{-4}$ mole) and 4-nitrobenzoyl chloride (0.21 g, 1.13×10$^{-3}$ mole) in methylene chloride (50 ml) was added triethylamine (1 ml). The reaction mixture was refluxed for 90 minutes. After cooling the mixture was poured into water (250 ml) and extracted with saturated aqueous sodium bicarbonate, then water, dried over magnesium sulfate, filtered and evaporated. The resulting oil, was crystallized from toluene and recrystallized from toluene-petroleum ether to afford the ester as white crystals (0.15 g, 71%) m.p. 160°-161° C. I.R. (nat): 3435 (NH), 1730 (C=O), 1610, 1588 (Ar-NO$_2$), 1305 (CF$_3$), 1261 (C-O), and 1112 cm$^{-1}$ (—O—CH$_2$—C).

EXAMPLE 17

Synthesis of
1,22-(l-dinitrophenylalanyl)-10,12-docosadiyne

To a solution of N-dinitrophenyl-l-alanine (0.166 g) and 0.104 gm of 10,12 docosadiyne-1,22 diol in 10 ml of DMSO at room temperature was added 0.005 gm of dimethylamino pyridine. A solution of N,N'-dicyclohexyl carbodiimide (0.129 g) in 10 ml of DMSO was added to the reaction mixture. After stirring for 4 hrs. at room temperature the mixture was poured into water and extracted with chloroform. The chloroform solution was washed with sodium bicarbonate, dried (MgSO$_4$) and evaporated. The product was chromatographed on silica and recrystallized from toluene-petroleum ether to yield 0.123 g of yellow needles which melted at 100° C.

What is claimed is:

1. An article comprising:
   at least one layer of at least one substantially polymerized diacetylene, said diacetylene being crystallizable into a crystal having a non-centrosymmetric unit cell; and means for establishing an electric field across said layer.

2. The article of claim 1 wherein said layer comprises an optical wave guide.

3. The article of claim 2 further comprising input means for coupling light into said layer and output means for coupling light out of said layer.

4. The article of claim 3 further comprising sensing means for detecting light transmitted by said layer.

5. An optical wave guide comprising at least one layer of a substantial polymerized diacetylene.

6. The article of claim 5 wherein said diacetylene is non-centrosymmetric.

7. The article of claim 5 wherein said diacetylene has at least one chiral center.

8. The article of claim 5, 6 or 7 having a sensible nonlinear optic effect.

9. An optical waveguide comprising at least one diacetylenic layer comprising at least one substantially polymerized diacetylene, at least one boundary layer on either side of said diacetylenic layer, said boundary layers having an index of refraction lower than said diacetylenic layer, and input means for coupling light into said diacetylenic layer.

10. The waveguide of claim 9 further comprising output means for coupling light out of said diacetylenic layer and sensing means for detecting light transmitted by said layer.

11. An apparatus comprising at least one nonlinear optical device comprising:
    a planar optical waveguide comprising at least one layer of a substantially polymerized diacetylene, said diacetylene being crystallizable into a crystal having a non-centrosymmetric unit cell;
    input means for coupling light into said waveguide; and
    output means for coupling light out of said waveguide.

12. The apparatus of claim 11 wherein the frequency of the light exiting the guide is a second harmonic of the frequency of the light entering the guide.

13. The apparatus of claim 12 wherein said exiting light is phase matched.

14. The apparatus of claim 11 further comprising means for establishing an electric field across said waveguide.

15. The apparatus of claim 14 wherein the light exiting the waveguide is modulated, polarized, frequency selected, amplified or frequency modified with respect to the light entering the waveguide.

16. The apparatus of claim 11 wherein said device is elaborated upon a substrate having semiconducting properties.

17. The apparatus of claims 11, 12, 13, 14, or 15 comprising a plurality of said nonlinear optical devices.

* * * * *